United States Patent [19]
Rappe

[11] Patent Number: 5,387,219
[45] Date of Patent: Feb. 7, 1995

[54] MEDICAL RETRIEVAL SNARE WITH COIL WRAPPED LOOP

[75] Inventor: Alan H. Rappe, Sun Prairie, Wis.

[73] Assignee: Target Therapeutics, Fremont, Calif.

[21] Appl. No.: 175,500

[22] Filed: Dec. 30, 1993

Related U.S. Application Data

[63] Continuation of Ser. No. 950,263, Sep. 23, 1992, abandoned.

[51] Int. Cl.$^6$ .................. A61B 19/00; A61B 17/22
[52] U.S. Cl. .................. 606/108; 606/1; 606/113
[58] Field of Search ............ 128/657, 772; 604/264, 604/280–282; 606/1, 106, 108, 110, 113, 114, 127, 128, 190, 192–194, 205–210

[56] References Cited

U.S. PATENT DOCUMENTS

| | | | |
|---|---|---|---|
| 3,452,740 | 7/1969 | Muller | 128/772 |
| 3,612,058 | 10/1971 | Ackerman | 128/772 |
| 3,739,784 | 6/1973 | Itoh | 606/113 |
| 4,579,127 | 4/1986 | Haacke | 128/772 |
| 4,798,586 | 1/1989 | Stevens | 606/108 |
| 4,884,579 | 12/1989 | Engelson | 128/657 |
| 5,045,061 | 9/1991 | Seifert et al. | 606/194 |
| 5,098,440 | 3/1992 | Millstead | 606/108 |
| 5,108,406 | 4/1992 | Lee | 606/113 |
| 5,108,407 | 4/1992 | Geremia et al. | 606/108 |
| 5,122,147 | 6/1992 | Sewell | 606/113 |
| 5,123,906 | 6/1992 | Kelman | 606/113 |

Primary Examiner—Stephen C. Pellegrino
Assistant Examiner—Glenn K. Dawson
Attorney, Agent, or Firm—Morrison & Foerster

[57] ABSTRACT

A device for retrieving foreign bodies, such as a vasoocclusive coil or elements, from within vessels such as those of the cardiovascular system includes a tubular member and a flexible wire that extends axially through the tubular member with its distal end extending out the distal end of the tubular member and looped back and affixed to the distal end of the tubular member to form a loop whose size may be adjusted by axial movement of the wire relative to the tubular member and which may be used to ensnare the foreign bodies and remove them from the vessel.

12 Claims, 3 Drawing Sheets

U.S. Patent  Feb. 7, 1995  Sheet 1 of 3  5,387,219

MEDICAL RETRIEVAL SNARE WITH COIL WRAPPED LOOP

This is a continuation of application Ser. No. 07/950,263, filed Sep. 23, 1992 now abandoned.

TECHNICAL FIELD

This invention relates to a device for capturing and removing bodies or articles from within a vessel, such as those of the cardiovascular system or the genitourinary tract.

BACKGROUND

Various loops and basket configurations have been used to remove calculi from the biliary or urinary system. See, for instance, U.S. Pat. No. 5,064,428.

Embolization of vessels is becoming of increasing therapeutic importance in treating conditions such as arteriovascular malformations, aneurysms, fistulas, vascular tumors, and the like. The procedure involves placing foreign bodies such as metal coils, balloons, beads, and the like into the vessel. At times these bodies become errant or it is desired to retrieve and remove them from the vessel for other reasons. Existing snares are too stiff and/or too large to permit deep tissue access through tortuous vessel paths. The present invention provides a device for retrieving bodies or articles from either tortuous vascular structures or larger vessels, organs, or ducts. Also, the distal structure of the device of the present invention can act to some degree like a guidewire, thus enabling the device to be somewhat guidewire directed. In contrast, existing snare devices cannot be directed like a guidewire.

DISCLOSURE OF THE INVENTION

The invention is a medical retrieval device for capturing and removing a body from within a vessel comprising:

(a) a first elongated member having a proximal end, a distal end, and a lumen extending therebetween, said first elongated member being capable of being advanced through the vessel to the site of the body; and (b) a second elongated member having a proximal end and a flexible distal end that is received through the lumen with the distal end of the second elongated member extending distally of the lumen and being looped back and affixed to the distal end of the first elongated member to form a loop whose size may be adjusted by axial movement of the second elongated member.

MODES FOR CARRYING OUT THE INVENTION

Figure 1:
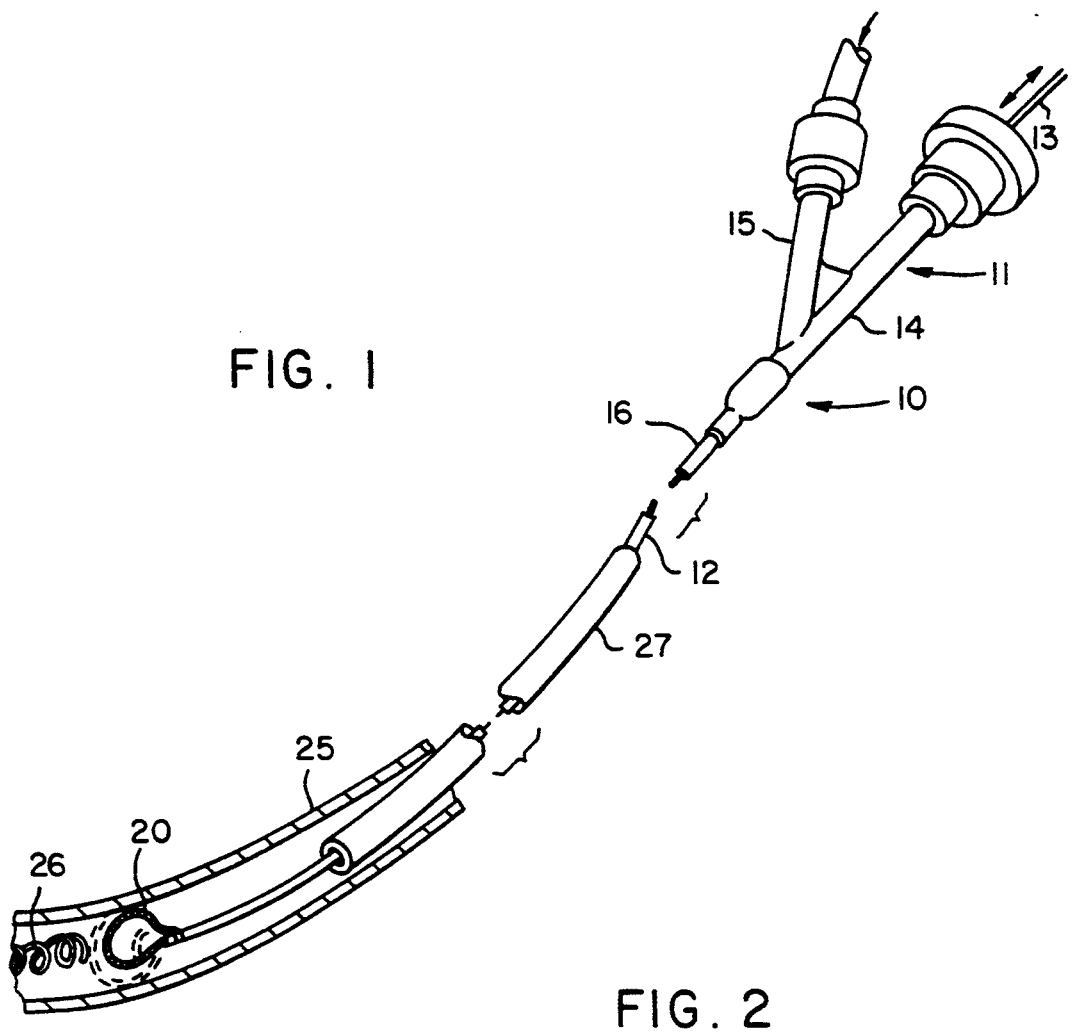
FIG. 1 is a fragmentary, partly sectional view of the device of the invention.
Figure 2:
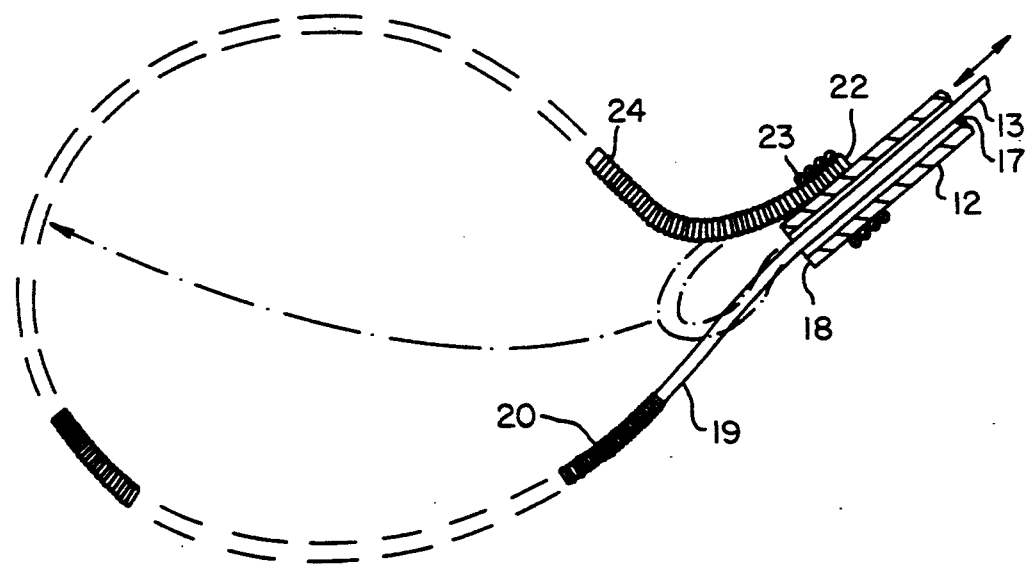
FIG. 2 is an enlarged sectional view of the distal end of the device of claim 1.

FIGS. 1 and 2 depict a preferred embodiment of the retrieval device of the invention. The retrieval device as a whole is generally designated 10. Its principal components are: a proximal end fitting 11; a catheter tube 12; and a flexible wire 13 that extends axially through the fitting and catheter tube.

Fitting 11 has a conventional structure that is commonly used at the proximal end of a catheter. It has a main body and an integral side arm 15. The main body 14 has a central axial lumen through which the flexible wire 13 is received. The side arm has a lumen which connects into the lumen of the main body. The proximal end of the side arm is connected to a source (not shown) of a physiologically acceptable fluid. The source preferably provides the fluid under pressure. Typically the fluid will be introduced into the side arm via a syringe or a tube connected to a pressurized intravenous fluid bag (not shown) connected thereto.

The proximal end 16 of catheter 12 is connected to the distal end of fitting 11 with the lumen 17 of the catheter communicating with the lumen of main body 14. The structure and size of catheter 12 is such as to permit it to be inserted within the small vessels of the peripheral vascular system. Preferably the catheter is of the structure and size described in U.S. Pat. No. 4,955,862, the disclosure of which is incorporated herein by reference.

Figure 4:
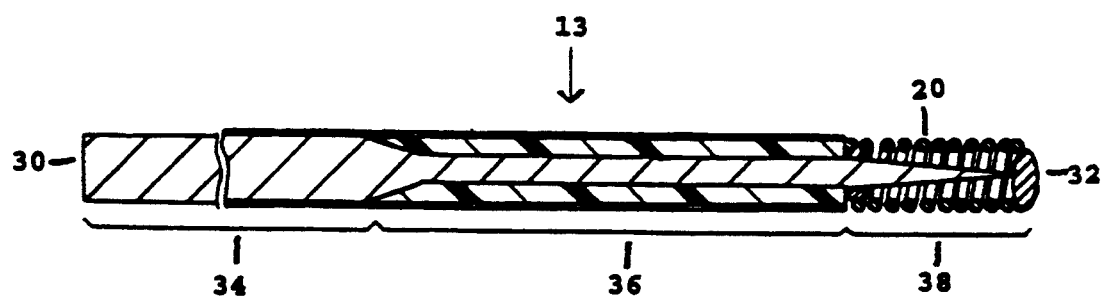
FIG. 4 is a fragmentary, partly section view of a guidewire accordingly to one embodiment of the invention.

Wire 13 extends axially through the entire length of catheter and extends out of the distal end 18 (see FIG. 2) of the catheter. The structure and dimensions of wire 13 are similar to those of a, conventional guidewire. Preferably wire 13 has the structure and dimensions of the guidewire described in U.S. Pat. No. 4,884,579, the disclosure of which is incorporated herein by reference. FIG. 4 shows a guidewire 13 according to U.S. Pat. No. 4,884,579. The wire is a flexible torqueable wire having an overall length of between about 70–300 cm between its proximal and distal ends 30, 32, respectively, and a maximum outer diameter of between about 8–40 mils (thousandths of an inch). The major portion of the wire is a flexible proximal section 34 whose overall length ranges from about 40–250 cm. The section 34 is followed by a more flexible intermediate section 36 having a diameter of between about 4–20 mils. and length between about 15–60 cm, and a most flexible distal end section 38 whose length is between about 1–10 cm. The wire core in the distal section 38, has a diameter which is substantially no greater than that of the intermediate section, and preferably is tapered to a reduced diameter of between about 2–6 mils. The distal end 19 of the wire is wrapped with a wire coil 20. The coil may be made of any conventional medically acceptable metal such as stainless steel, tungsten, platinum, platinum alloys, gold and gold alloys. The use of a radiopaque metal makes the end visible radiographically. Coil 20 serves to protect the distal end 19 from kinking when it is manipulated. Typically about 0.5 to 20 cm of the distal end will be wrapped with coil. The distal tip 22 of the wire is affixed to the exterior of the distal end of the catheter by means of a tightly wrapped metal coil 23 or metal band that extends around the circumference of the tip of the catheter. It may also be affixed to the interior wall of the catheter provided the lumen is large enough to permit same, or it may be affixed to coil 23 by solder and/or to the catheter wall by fusion with the plastic forming the catheter. Coil 23 is preferably made of a radiopaque metal such as platinum so that the location of the end of the catheter is visible radiographically. In the event coil 23 does not serve as a radiopaque marker, a separate radiopaque band or coil may be affixed to the tip of the catheter. The affixation of the tip of wire 13 to the catheter forms the distal end of the wire into a loop 24, the size of which may be altered by axial movement (represented by the double-headed arrow in FIGS. 1 and 2) of wire 13. The extended configuration of loop 24 is shown in solid and dashed lines in FIG. 2 and the retracted configuration of loop 24 is shown in phantom lines in FIG. 2.

Figure 3A:
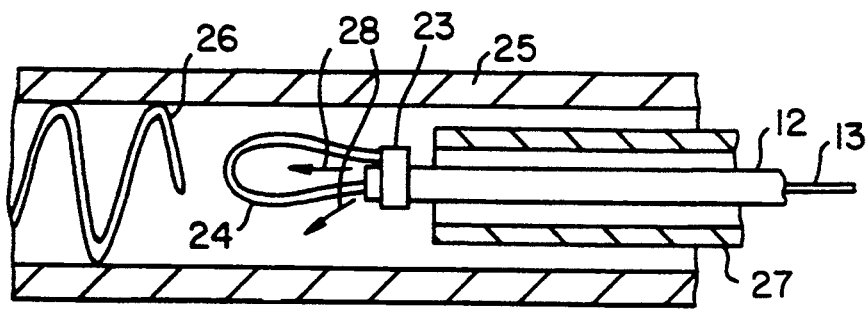
FIGS. 3A–3D are enlarged sectional partial views of the device of FIG. 1 depicting the operation of the device.
Figure 3B:
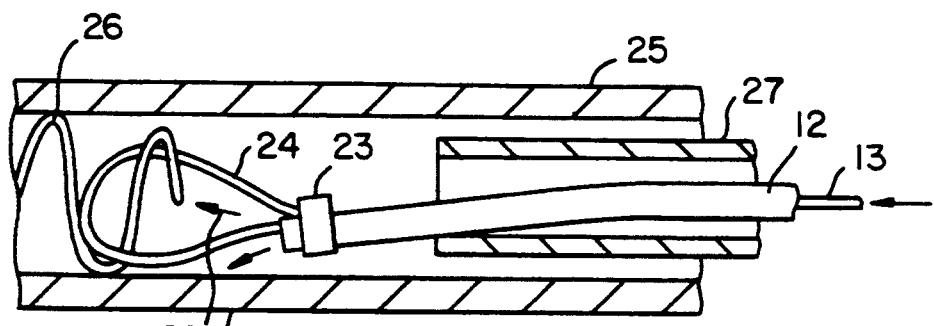
Figure 3C:
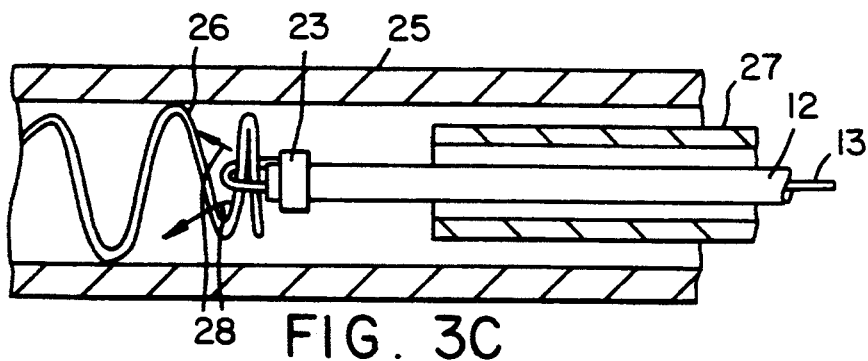
Figure 3D:
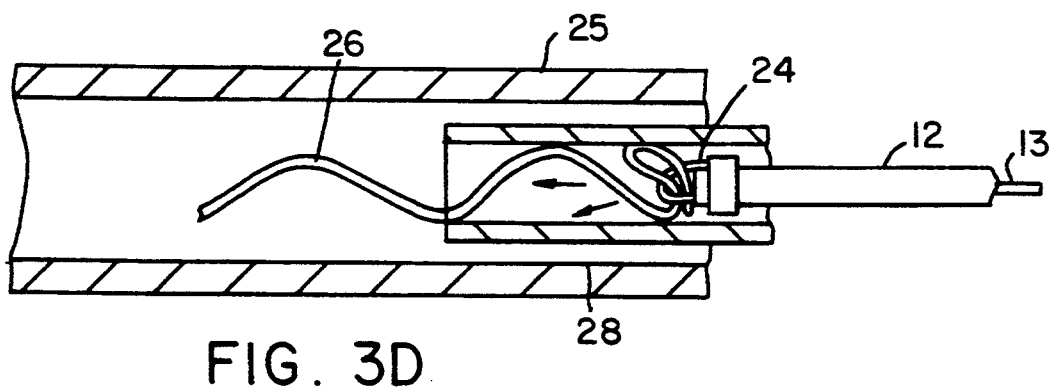

FIGS. 1 and 3A-D show how the retrieval device is used to retrieve a body from within a vessel. As seen in FIGS. 1 and 3A, the device is inserted into a vessel 25 so that the distal end of the device is adjacent to the body to be removed from the vessel—in the depicted case a vasoocclusive coil 26. The insertion of the device to such a location is accomplished in a conventional manner. Insertion can be facilitated by alternately advancing and withdrawing the loop—i.e., using the loop as a guidewire. If desired a larger catheter 27 may be placed in the vessel using a separate guidewire (not shown) and the catheter-wire assembly of the invention inserted to the site via catheter 27. Once the device is so positioned loop 24 of the device is enlarged by distal advancement of wire 13 while holding catheter 12 stationary. In order to facilitate the axial manipulation of wire 13 within tube 12, a physiologically acceptable fluid (represented by arrows 28 in FIGS. 3A-3D) may be pumped through the lumen of catheter 12 from side arm 15—thus providing lubrication between the wire and the catheter. Loop 24 is manipulated within the vessel to ensnare (see FIG. 3B) coil 26. Once the coil is ensnared, the loop 24 is retracted (see FIG. 3C) by proximal movement of wire 13 so that the coil 26 is held firmly by the loop against the tip of the catheter. The thus captured and firmly-held coil 26 is removed from the vessel by withdrawing the catheter-wire assembly from the vessel (see FIG. 3D) or into catheter 27.

Modifications of the above-described modes for carrying out the invention that are obvious to those of skill in the medical device art are intended to be within the scope of the following claims.

I claim:

1. A medical retrieval device for capturing and removing a body from a site within a vessel comprising:
   (a) a first elongated member having a proximal end, a distal end, and a lumen extending therebetween, said first elongated member being capable of being advanced through the vessel to the site of the body; and
   (b) a second elongated member having a proximal end and a distal end that is received through the lumen of the first elongated member with the distal end of the second elongated member extending distally of the distal end of the first elongated member and being looped back and affixed to the distal end of the first elongated member to form a loop whose size may be adjusted by longitudinal movement of the second elongated member relative to the first member;
   said second elongated member having (i) a flexible proximal section between about 50-250 cm in length and having an outer diameter of between about 10-40 mils, (ii) a more flexible intermediate section having a length between about 20-60 cm and having a diameter of between about 4-20 mils, and (iii) a most flexible distal end section having a length between about 1-10 cm and having a diameter of between about 2-6 mils; at least a portion of said distal end section being wrapped with coil.

2. The device of claim 1 including (c) a radiopaque marker member carried on the distal end of the first elongated member.

3. The device of claim 2 wherein the radiopaque marker member is made of metal.

4. The medical retrieval device of claim 2 wherein the distal end of the second elongated member is affixed to the exterior of the distal end of the first elongated member.

5. The medical retrieval device of claim 1 including means on said proximal end of the first elongated member for passing a physiologically acceptable fluid in a distal direction through said lumen to provide lubrication between the first elongated member and second elongated member.

6. The medical retrieval device of claim 5 wherein said means for passing includes a proximal end fitting to which the proximal end of the first elongated member is attached, said proximal end fitting having an axial lumen that communicates with the lumen of the first elongated member and through which the second elongated member extends and through which said physiologically acceptable fluid is adapted to flow.

7. A medical retrieval device for capturing and removing a body from a site within a vessel comprising:
   (a) a catheter body having a proximal end, a distal end, and a lumen extending therebetween, said catheter body being capable of being advanced through the vessel to the site of the body; and
   (b) an elongated member having a proximal end and a distal end that is received through the lumen of the catheter body with the distal end of the elongated member extending distally of the distal end of the catheter body and being looped back and directly affixed to the distal end of the catheter body to form a loop whose size may be adjusted by longitudinal movement of the elongated member relative to the catheter body;
   said elongated member having (i) a flexible proximal section between about 50-250 cm in length and having an outer diameter of between about 10-40 mils, (ii) a more flexible intermediate section having a length between about 20-60 cm and having a diameter of between about 4-20 mils, and (iii) a most flexible distal end section having a length between about 1-10 cm and having a diameter of between about 2-6 mils; at least a portion of said distal end section being wrapped with coil.

8. The device of claim 7 further including (c) a radiopaque marker member carried on the distal end of the catheter body.

9. The device of claim 8 where the radiopaque marker member is made of metal.

10. The device of claim 7 where the distal end of the elongated member is affixed to the exterior of the distal end of the catheter body.

11. The device of claim 7 including means on the proximal end of the catheter body for passing a physiologically acceptable fluid in a distal direction through the catheter body lumen to provide lubrication between the catheter body and the elongated member.

12. The device of claim 11 where said means includes a proximal end fitting to which the proximal end of the catheter body is attached, said end fitting having an axial lumen that communicates with the catheter body lumen and through which the elongated member extends and through which the said physiologically acceptable fluid is adapted to flow.

* * * * *